United States Patent [19]
Syvret

[11] Patent Number: 5,939,546
[45] Date of Patent: Aug. 17, 1999

[54] IMIDAZOLATE SULFURYL DIFLUORIDES

[75] Inventor: Robert George Syvret, Allentown, Pa.

[73] Assignee: Air Products and Chemicals, Inc., Allentown, Pa.

[21] Appl. No.: 09/020,582

[22] Filed: Jan. 30, 1998

[51] Int. Cl.[6] ............ C07D 413/00; C07D 403/12; C07D 233/60; C09K 3/00
[52] U.S. Cl. ............ 544/139; 252/182.15; 548/110; 548/313.7; 548/325.1
[58] Field of Search ............ 548/313.7, 325.1; 544/139

[56] References Cited

U.S. PATENT DOCUMENTS

| | | | |
|---|---|---|---|
| 3,888,924 | 6/1975 | Middleton | 260/543 |
| 3,914,265 | 10/1975 | Middleton | 260/397 |
| 3,933,819 | 1/1976 | Tourkan et al. | 548/325.1 |
| 3,976,691 | 8/1976 | Middleton | 260/544 |
| 4,351,946 | 9/1982 | Toukan et al. | 548/325.1 |

FOREIGN PATENT DOCUMENTS

| | | |
|---|---|---|
| 433136 | 12/1974 | U.S.S.R. . |

OTHER PUBLICATIONS

G.C. Demitras, R.A. Kent, and A.C. MacDiarmid, Chem. Ind. (London) (1964), p. 1712.

G.C. Demitras and A.C. MacDiarmid. Inorg. Chem. (1967), 6, pp. 1903–1906.

S.P. Von Halasz and O. Glemser, Chem. Ber. (1971), 104, pp. 1247–1255.

L.N. Markovskij, V.E. Pashinnik and A.V. Kirsanov, Synthesis, (1973), pp. 787–789.

W.J. Middleton, J. Org. Chem. (1975), 40, pp. 574–578.

L.N. Markovskij, V.E. Pashinnik, A.V. Kirsanov, Zh. Org. Khim. (1975), 11(1) pp. 72–74.

L.N. Markovskij, V.E. Pashinnik, A.V. Kirsanov, Zh. Org. Khim. (1976), 12(5) pp. 973–974.

R.E. Wasylishen, G.S. Birdi, A.F. Janzen, Inorg. Chem. (1976), 15(12), pp. 3054–3056.

A.F. Janzen, G.N. Lypka, R.E. Wasylishen, Can. J. Chem. (1980), 58, pp. 60–64.

B.E. Cooper, Chem. Ind. (1978), pp. 794–797.

C.A. Bruynes, T.K. Jurriens, J. Org. Chem. (1982), 47, pp. 3966–3969.

D.N. Harpp, K. Steliou, T.H. Chan, J. Am. Chem. Soc. (1978), 100(4), pp. 1222–1228.

S. Berner, K. Muehlegger, H. Seliger, Nuc. Ac. Res. (1989), 42, pp. 853–864.

P.A. Messina, K.C. Mange, W.J. Middleton, J. Fluorine Chem. (1989), 42, pp. 137–143.

*Primary Examiner*—Floyd D. Higel
*Attorney, Agent, or Firm*—Geoffrey L. Chase

[57] ABSTRACT

Imidazole sulfuryldifluoride compositions are disclosed as useful deoxofluorination reagents.

11 Claims, No Drawings

# IMIDAZOLATE SULFURYL DIFLUORIDES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The development of safe, efficient, and simple methods for selective incorporation of fluorine into organic compounds has become a very important area of technology. This is due to the fact that fluorine strategically positioned at sites of synthetic drugs and agrochemical products significantly modifies and enhances their biological activities. The conversion of the C—O to the C—F bond, which is referred to here as a deoxofluorination, represents a viable method to produce selectively fluorinated organic compounds, but the low yields and hazards associated with the current deoxofluorination reagents and processes severely limit the application of this technique.

The introduction of fluorine into medicinal and agrochemical products can profoundly alter their biological properties. Fluorine mimics hydrogen with respect to steric requirements and contributes to an alteration of the electronic properties of the molecule. Increased lipophilicity and oxidative and thermal stabilities have been observed in such fluorine-containing compounds.

In view of the importance of organofluorine compounds, efforts aimed at the development of simple, safe, and efficient methods for their synthesis have escalated in recent years. The conversion of the carbon-oxygen to the carbon-fluorine bond by nucleophilic fluorinating sources (deoxofluorination) represents one such technique which has been widely used for the selective introduction of fluorine into organic compounds. A list of the deoxofluorination methods practiced to date includes: nucleophilic substitution via the fluoride anion; phenylsulfur trifluoride; fluoroalkylamines; sulfur tetrafluoride; $SeF_4$; $WF_6$; difluorophosphoranes and the dialkylaminosulfur trifluorides (DAST). The most common reagent of this class is diethylaminosulfur trifluoride, Et-DAST or simply DAST.

Compounds containing the $NSF_3$ moiety were first reported in the late 1960s; G. C. Demitras, R. A. Kent, and A. C. MacDiarmid, Chem. Ind. (London) (1964), p1712; G. C. Demitras and A. C. MacDiarmid, Inorg. Chem. (1967), 6, pp1903–1906 and early 1970s; S. P. Von Halasz and O. Glemser, Chem. Ber. (1971), 104, pp1247–1255, however, their use as deoxofluorination agents was not disclosed in these citations. It wasn't until the work of Markovskij et al.; L. N. Markovskij, V. E. Pashinnik, and A. V. Kirsanov, Synthesis, (1973), pp787–789 that the dialkylaminosulfur trifluoride compounds were first shown to be effective fluorinating agents for a wide range of organic substrates. Following this initial report, two patents; W. J. Middleton, U.S. Pat. No. 3,914,265 and W. J. Middleton, U.S. Pat. No. 3,976,691 and a publication; W. J. Middleton, J. Org. Chem. (1975), 40, pp574–578 appeared which fully disclosed the utility of these new compounds in deoxofluorination type reactions.

The analogous $SF_2$ compounds were actually reported in the literature; the Middleton article immediately above and L. N. Markovskij, V. E. Pashinnik, A. V. Kirsanov, Zh. Org. Khim. (1975), 11(1) pp72–74 and in a patent; W. J. Middleton, U.S. Pat. No. 3,888,924. The $SF_2$ compounds are also know to function as deoxofluorination agents.

The various $SF_3$ compounds were first prepared through the reactions of $SF_4$ with the corresponding trimethylsilylated amine, $(Me)_3SiNRR'$ in accordance with the literature set forth above, but have also been successfully made by the direct reaction of $SF_4$ with the free amine, RR'NH, in the presence of an HF scavenger; L. N. Markovskij, V. E. Pashinnik, A. V. Kirsanov, USSR Patent 433136 (Application No. 1864289/234) or the sulfoxide of the amine, $R_2NS(O)R'$, with concomitant formation of the sulfinic fluoride, R'S(O)F; L. N. Markovskij, V. E. Pashinnik, A. V. Kirsanov, Zh. Org. Khim. (1976), 12(5) pp973–974. Similarly, the previously known $SF_2$ compounds have been prepared through the reaction of the corresponding $SF_3$ compound, $RR'NSF_3$, with either a second molecule of the trimethylsilylated amine, $(Me)_3SiNRR'$ in accordance with the above literature, or a molecule of a diaminosulfinate, $R_2"NS(O)NR_2"$ in accordance with Markovshkij, et. al., immediately above.

The methods of preparation for trimethylsilylated imidazole derivatives are available in the literature; R. E. Wasylishen, G. S. Birdi, A. F. Janzen, Inorg. Chem. (1976), 15(12), pp3054–3056; A. F. Janzen, G. N. Lypka, R. E. Wasylishen, Can. J. Chem. (1980), 58, pp60–64; B. E. Cooper, Chem. Ind. (1978), pp794–797; C. A. Bruynes, T. K. Jurriens, J. Org. Chem. (1982), 47, pp3966–3969; D. N. Harpp, K. Steliou, T. H. Chan, J. Am. Chem. Soc. (1978), 100(4), pp1222–1228; and S. Berner, K. Muehlegger, H. Seliger, Nuc. Ac. Res. (1989), 17(3), pp853–864.

All of the known compositions described so far are widely regarded as effective deoxofluorination agents, but are as equally regarded as being inherently unsafe in their use because of their propensity to undergo catastrophic decomposition reactions when heated. In fact, a study, P. A. Messina, K. C. Mange, W. J. Middleton, J. Fluorine Chem. (1989), 42, pp137–143, of the thermal properties of some of the more popular of these compositions measured by differential thermal analysis (DTA) concluded that even the most stable of all compositions, 4-morpholinosulfur trifluoride, will detonate at 175° C. Furthermore, in the same study, some of the even lesser stable bis(dialkylamino)sulfur difluoride derivatives were shown to be detonators at much lower temperatures than their sulfur trifluoride analogues, e.g., bis(diethylamino)sulfur difluoride detonated at 108° C. while diethylaminosulfur trifluoride detonated at 147° C.

The compositions of the present invention overcome the drawbacks of the prior art fluorinating agents, including DAST, by providing more thermally stable fluorine bearing compounds which have effective fluorinating capability with far less potential of violent decomposition and attendant high gaseous by-product evolvement, as will be set forth in greater detail below.

BRIEF SUMMARY OF THE INVENTION

The present invention is a compound having the structure:

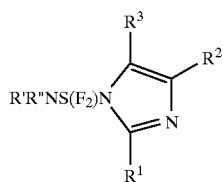

wherein $R^{1-3}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof; and $R^{2-3}$ together selected from the group consisting of:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical;

wherein R' and R" are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl or taken together with the nitrogen group form a saturated cyclic ring having 2–10 carbon ring members and 0–2 heteroatoms selected from the group consisting of oxygen, nitrogen, sulfur, and mixtures thereof; and further R' and R" together are an imidazole ring of the formula:

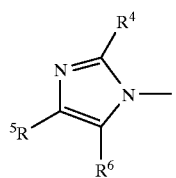

having $R^{4-6}$ which are the same or different than $R^{1-3}$ on the other imidazole ring and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof; and $R^{5-6}$ together selected from the group consisting of:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon a toms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

Preferably, the compound has the structure:

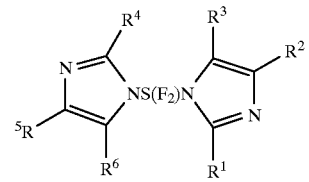

wherein $R^{1-6}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof; and $R^{2-3}$ and $R^{5-6}$ respectively selected from the group consisting of:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

More preferably, the compound is 1,1'-Di(imidazole) Sulfinyl Difluoride.

Alternatively, the compound is 1,1'-Di(4-phenylimidazole)Sulfinyl Difluoride

Further alternatively, the compound is 1-morpholino-1'-imidazole sulfinyl difluoride.

In addition, the present invention is also a method for fluorination of a first compound using a fluorinating reagent comprising contacting said first compound with said fluorinating reagent under conditions sufficient to fluorinate said first compound wherein said fluorinating reagent is a second compound having the structure:

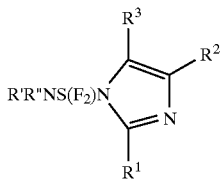

wherein $R^{1-3}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof; and $R^{2-3}$ together selected from the group consisting of:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical;

wherein R' and R" are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl or taken together with the nitrogen group form a saturated cyclic ring having 2–10 carbon ring members and 0–2 heteroatoms selected from the group consisting of oxygen, nitrogen, sulfur, and mixtures thereof; and R' and R" together are an imidazole ring of the formula:

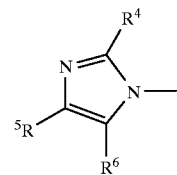

having $R^{4-6}$ which are the same or different than $R^{1-3}$ on the other imidazole ring and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof; and $R^{5-6}$ together selected from the group consisting of:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

In one alternative, the method uses a composition having the structure:

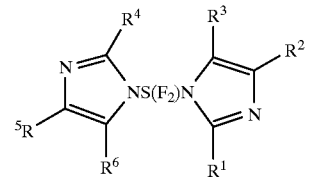

wherein $R^{1-6}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof; and $R^{2-3}$ and $R^{5-6}$ respectively selected from the group consisting of:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

Preferably, the first compound is selected from the group consisting of alcohols, carboxylic acids, aldehydes, ketones, carboxylic acid halides, sulfoxides, phosphonic acids, sulfinyl halides, sulfonoic acids, sulfonylhalides, silylhalides, silylethers of alcohols, epoxides, phosphines, thiophosphines, sulfides and mixtures thereof.

More preferably, the second compound used in the method is 1,1'-Di(imidazole)sulfinyl Difluoride.

Alternatively the second compound used in the method is 1,1'-Di(4-phenylimidazole)Sulfinyl Difluoride Further alternatively, the second compound used in the method is 1-morpholino-1'-imidazole sulfinyl difluoride.

BRIEF DESCRIPTION OF SEVERAL VIEWS OF THE DRAWINGS

Not Applicable

DETAILED DESCRIPTION OF THE INVENTION

The present invention relates to a family of new sulfur (IV) difluoride compositions which are effective deoxofluorination agents, i.e., can be used to convert R—OH to R—F, RC(O)R' to RCF2R', and RC(O)H to RCF2H, and which are safe to handle and use. These compounds are easily handled solids which melt at high temperature and are thermally stable beyond their melting points. Thermal decomposition of these compounds occurs slowly and without the rapid release of gaseous by-products which is generally associated with explosive materials. Hence, by comparison to other similar sulfur-fluorine compounds wherein the decomposition is generally accompanied by a rapid and uncontrollable release of gaseous pressure, these new compositions are inherently much safer to handle and use.

Aminosulfur trifluoride compounds are recognized as deoxofluorination agents, but as the literature above indicates are also recognized as being inherently unsafe in their use because of their propensity to undergo catastrophic decomposition reactions when heated. The less stable bis (dialkylamino)sulfur difluoride derivatives were shown to be detonators at much lower temperatures than their sulfur trifluoride analogues, e.g., bis(diethylamino)sulfur difluoride detonated at 108° C. while diethylaminosulfur trifluoride detonated at 147° C.

The above cited thermal study of Messina, et. al. was performed using the DTA technique and employed 1 mmol of sample and a heating rate of 20° C./min. The very small sample size combined with the relatively high heating rate leads one to suspect that the "actual" decomposition temperatures for these compound may indeed be significantly lower.

In the course of the present work, using a more sensitive thermal analytical method (than DTA), *the Radex-Solo Thermal Screening Method*, which employs a larger sample size and measures pressure generated and sample temperature during decomposition, we have measured the onset temperature for thermal decomposition and pressure generated of three of the most popular aminosulfur trifluoride compounds. In addition, two representative "$SF_2$" compositions of the present invention have been measured under the same conditions. These results are summarized in Table 1.

TABLE 1

Results for Radex-Solo Thermal Screening Method Measurements for Three Aminosulfur Trifluoride Compounds

| Compound | sample size, mg (mmol) | max temp rate of decomposition (° C./min) | max pressure rate of decomposition (psi/min) |
|---|---|---|---|
| dimethylaminosulfur trifluoride | 680 (5.1) | 114.2 | 16396 |
| 4-morpholinosulfur trifluoride | 470 (2.7) | 70.8 | 10275 |
| diethyaminosulfur trifluoride | 776 (4.8) | 173.6 | 15707 |
| bis(imidazole)sulfur difluoride | 266 (1.3) | 20.7 | 719 |
| bis(4-phenylimidazole)-sulfur difluoride | 558 (1.6) | 24.7 | 731 |

A comparison of the Radex data for the three $SF_3$ literature compounds with the data for the two $SF_2$ compounds of the present invention reveals two profound differences. First, in terms of the maximum temperature rate during decomposition, the three $SF_3$ compounds exhibit a much greater rate than either of the $SF_2$ compounds which indicates that the decomposition events of the former are much faster than the later. Secondly, the pressure rate generated during decomposition of the $SF_3$ compounds is at least an order of magnitude greater than either of the $SF_2$ compounds. This leads one to conclude that the decomposition events of the $SF_3$ compounds will be far more violent and certainly more consistent with an explosive event than the decomposition of either of the $SF_2$ compounds.

The present invention relates to new compounds containing the $SF_2$ moiety which are safe and effective deoxofluorination agents and are pictorially represented by either Structures (I) or (II).

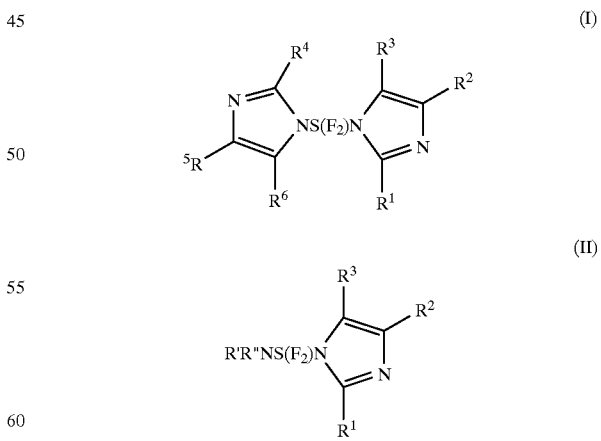

In the present invention, $R_1$, $R_2$, and $R_3$ are the same or different and need not be the same for both imidazole rings on the same —$SF_2$— Structure. Furthermore, R' and R" are the same or different independent groups or are jointly part of a fused ring substituent. Specifically, $R_1$ is selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, a $C_{4-8}$ saturated cyclic hydrocarbon having 1–3 heteroatoms selected from the group consisting of oxygen, nitrogen, sulfur, and mixtures thereof. $R_2$ and $R_3$ can specifically be any substituent defined for $R_1$ above, but in addition to these definitions, together are a cyclic ring having 2–10 carbon ring members and 1 heteroatom selected from the group consisting of oxygen, sulfur, nitrogen, $C_{1-3}$ alkylated nitrogen, protonated nitrogen i.e. hydrogenated, and halogenated nitrogen; or $R_2$ and $R_3$ together are an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or $R_2$ and $R_3$ taken together are a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical;

It should be understood that throughout this text, when a haloalkyl portion is defined as $C_{1-3}$, a alkoxy portion is defined as $C_{1-3}$, a haloalkoxy portion is defined as $C_{1-3}$, a haloaryl is defined as $C_{4-10}$, a heteroaryl is defined as $C_{4-10}$, and any analogous definitions, it is intended to mean that the radical will additionally include: (1) a halogen in the form of chlorine, bromine, iodine or fluorine in the case of the recitation of halo; (2) oxygen in the case of the recitation of oxy; (3) halogen and oxygen in the case of the recitation of halo and oxy in the same definition; and (4) nitrogen, oxygen and/or sulfur in the case of the recitation of hetero. For instance, where the haloalkyl portion is $C_{1-3}$, a representative radical would be $ClH_2CCH_2CH_2$—.

These new compounds are generally prepared in two steps as illustrated below in equation (1) and (2) for bis (imidazole)sulfur difluorides of compounds (I):

(1)

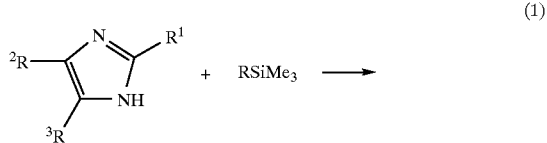

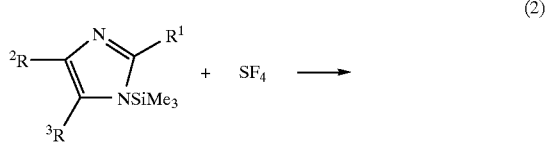

(2)

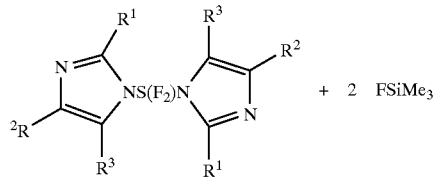

or alternately according to equation (3) for the general Structure(II):

(3)

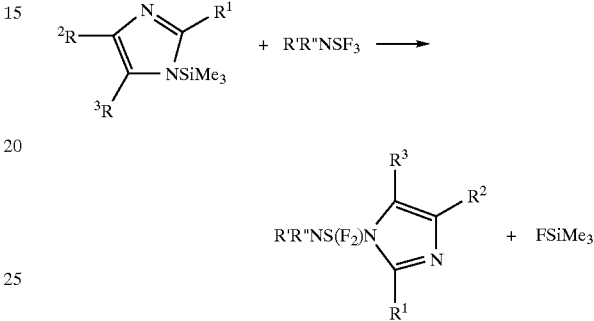

With regard to compounds of equation (I), the R groups on the two imidazole rings may differ merely by using a mixture of imidazole precursors.

Exemplary compounds of the equation (I) include the following compounds: 1,1'-diimidazole sulfinyl difluoride; 1,1'-(benzimidazole)imidazole sulfinyl difluoride; 1,1'-(2-methyl)diimidazole sulfinyl difluoride; 1,1'-(2-ethyl) diimidazole sulfinyl difluoride; 1,1'-(2-isopropyl) diimidazole sulfinyl difluoride; 1,1'-(2-phenyl)diimidazole sulfinyl difluoride; 1,1'-(2-fluoro)diimidazole sulfinyl difluoride; 1,1'-(2-methoxy)diimidazole sulfinyl difluoride; 1,1'-(2-ethoxy)diimidazole sulfinyl difluoride; 1,1'-(4-methyl)diimidazole sulfinyl difluoride; 1,1'-(4-ethyl) diimidazole sulfinyl difluoride; 1,1'-(4-phenyl)diimidazole sulfinyl difluoride; 1,1'-(4-(2-fluorophenyl))diimidazole sulfinyl difluoride; 1,1'-(4-(4-fluorophenyl))diimidazole sulfinyl difluoride; 1,1'-(4-(2,4-difluorophenyl))diimidazole sulfinyl difluoride; 1,1'-(4-(2- chlorophenyl))diimidazole sulfinyl difluoride; 1,1'-(4-(4-chlorophenyl))diimidazole sulfinyl difluoride; 1,1'-(4-(2,4-dichlorophenyl))diimidazole sulfinyl difluoride; 1,1'-(4-(4-methylphenyl))diimidazole sulfinyl difluoride; 1,1'-(4-(4-methoxyphenyl))diimidazole sulfinyl difluoride; 1,1'-(4-(4-nitrophenyl))diimidazole sulfinyl difluoride; 1,1'-(4-(4-aminophenyl))diimidazole sulfinyl difluoride; 1,1'-(4-fluoro)diimidazole sulfinyl difluoride; 1,1'-(4-chloro)diimidazole sulfinyl difluoride; 1,1'-(4-methoxy)diimidazole sulfinyl difluoride; 1,1'-(5-methyl) diimidazole sulfinyl difluoride; 1,1'-(5-ethyl)diimidazole sulfinyl difluoride; 1,1'-(5-phenyl)diimidazole sulfinyl difluoride; 1,1'-(5-fluoro)diimidazole sulfinyl difluoride; 1,1'-di(benzimidazole) sulfinyl difluoride; 1,1'-di(2-methylimidazole) sulfinyl difluoride; 1,1'-di(2-ethylimidazole) sulfinyl difluoride; 1,1'-di(2-n-propylimidazole) sulfinyl difluoride; 1,1'-di(2-isopropylimidazole) sulfinyl difluoride; 1,1'-di(2-phenylimidazole) sulfinyl difluoride; 1,1'-di(2-fluoroimidazole) sulfinyl difluoride; 1,1'-di(2-chloroimidazole) sulfinyl difluoride; 1,1'-di(2-methoxyimidazole) sulfinyl difluoride; 1,1'-di(2-ethoxyimidazole) sulfinyl difluoride; 1,1'-di(4- methylimidazole) sulfinyl difluoride; 1,1'-di(4-ethylimidazole) sulfinyl difluoride; 1,1'-di(4-phenylimidazole) sulfinyl difluoride; 1,1'-di(4-(2-fluorophenyl)imidazole) sulfinyl difluoride; 1,1'-di(4-(4-fluorophenyl)imidazole) sulfinyl difluoride; 1,1'-di(4-(2,4-difluorophenyl)imidazole) sulfinyl difluoride; 1,1'-di(4-pentafluorophenylimidazole) sulfinyl difluoride; 1,1'-di(4-(2-chlorophenyl)imidazole) sulfinyl difluoride; 1,1'-di(4-(4-chlorophenyl)imidazole) sulfinyl difluoride; 1,1'-di(4-(2,4-dichlorophenyl)imidazole) sulfinyl difluoride; 1,1'-di(4-(4-methylphenyl)imidazole) sulfinyl difluoride; 1,1'-di(4-(4-methoxyphenyl)imidazole) sulfinyl difluoride; 1,1'-di(4-(4-nitrophenyl)imidazole) sulfinyl difluoride; 1,1'-di(4-(4-aminophenyl)imidazole) sulfinyl difluoride; 1,1'-di(4-fluoroimidazole) sulfinyl difluoride; 1,1'-di(4-chloroimidazole) sulfinyl difluoride; 1,1'-di(5-methylimidazole) sulfinyl difluoride; 1,1'-di(5-phenylimidazole) sulfinyl difluoride; 1,1'-di(5-fluoroimidazole) sulfinyl difluoride; 1,1'-(2,4-dimethyl)diimidazole sulfinyl difluoride; 1,1'-(2,4-diphenyl)diimidazole sulfinyl difluoride; 1,1'-(2,4-difluoro)diimidazole sulfinyl difluoride; 1,1'-(2,4-dichloro)diimidazole sulfinyl difluoride; 1,1'-(2,5-dimethyl)diimidazole sulfinyl difluoride; 1,1'-(2,5-diethyl)diimidazole sulfinyl difluoride; 1,1'-(2,5-diphenyl)diimidazole sulfinyl difluoride; 1,1'-(2,5-difluoro)diimidazole sulfinyl difluoride; 1,1'-(2,5-dichloro)diimidazole sulfinyl difluoride; 1,1'-(4,5-dimethyl)diimidazole sulfinyl difluoride; 1,1'-(4,5-dicyano)diimidazole sulfinyl difluoride; 1,1'-(4,5-diphenyl)diimidazole sulfinyl difluoride; 1,1'-(4,5-difluoro)diimidazole sulfinyl difluoride; 1,1'-(4,5-dichloro)diimidazole sulfinyl difluoride; 1,1'-(4,5-dimethoxy)diimidazole sulfinyl difluoride; 1,1'-di(2,4-dimethylimidazole) sulfinyl difluoride; 1,1'-di(2,4-diethylimidazole) sulfinyl difluoride; 1,1'-di(2,4-diphenylimidazole) sulfinyl difluoride; 1,1'-di(2,4-difluoroimidazole) sulfinyl difluoride; 1,1'-di(2,4-dichloroimidazole) sulfinyl difluoride; 1,1'-di(2,5-dimethylimidazole) sulfinyl difluoride; 1,1'-di(2,5-diphenylimidazole) sulfinyl difluoride; 1,1'-di(2,5-difluoroimidazole) sulfinyl difluoride; 1,1'-di(2,5-dichloroimidazole) sulfinyl difluoride; 1,1'-di(2,5-dimethylimidazole) sulfinyl difluoride; 1,1'-di(2,5-diphenylimidazole) sulfinyl difluoride; 1,1'-di(4,5-(2-fluorophenyl)imidazole) sulfinyl difluoride; 1,1'-di(4,5-(4-fluorophenyl)imidazole) sulfinyl difluoride; 1,1'-di(4,5-di(4-methylphenyl)imidazole) sulfinyl difluoride; 1,1'-di(4,5-di(4-methoxyphenyl)imidazole) sulfinyl difluoride; 1,1'-di(4,5-di(4-nitrophenyl)imidazole) sulfinyl difluoride; 1,1'-di(4,5-di(4-aminophenyl)imidazole) sulfinyl difluoride; 1,1'-di(4,5-difluoroimidazole) sulfinyl difluoride; 1,1'-di(4,5-dichloroimidazole) sulfinyl difluoride; 1,1'-di(4,5-dimethoxyimidazole) sulfinyl difluoride; 1,1'-(trifluoro)diimidazole sulfinyl difluoride 1,1'-di(trifluoro)imidazole sulfinyl difluoride; 1,1'-(trimethyl)diimidazole sulfinyl difluoride; and 1,1'-di(trimethyl)imidazole sulfinyl difluoride.

Exemplary compounds of equation (II) include the following compounds: 1-morpholino-1'-imidazole sulfinyl difluoride; 1-morpholino-1'-benzimidazole sulfinyl difluoride; 1-morpholino-1'-(2'-methylimidazole) sulfinyl difluoride; 1-morpholino-1'-(2'-ethylimidazole) sulfinyl difluoride; 1-morpholino-1'-(2'-isopropylimidazole) sulfinyl difluoride; 1-morpholino-1'-(2'-phenylimidazole) sulfinyl difluoride; 1-morpholino-1'-(2'-fluoroimidazole) sulfinyl difluoride; 1-morpholino-1'-(2'-chloroimidazole) sulfinyl difluoride; 1-morpholino-1'-(2'-methoxyimidazole) sulfinyl difluoride; 1-morpholino-1'-(4'-methylimidazole) sulfinyl difluoride; 1-morpholino-1'-(4'-phenylimidazole) sulfinyl difluoride; 1-morpholino-1'-(4'-(2-fluorophenyl)imidazole) sulfinyl difluoride; 1-morpholino-1'-(4'-(4-fluorophenyl)imidazole) sulfinyl difluoride; 1-morpholino-1'-(4'-(2,4-difluorophenyl)imidazole) sulfinyl difluoride; 1-morpholino-1'-(4'-(4-methylphenyl)imidazole) sulfinyl difluoride; 1-morpholino-1'-(4'-(4-methoxyphenyl)imidazole) sulfinyl difluoride; 1-morpholino-1'-(4'-(4-nitrophenyl)imidazole) sulfinyl difluoride; 1-morpholino-1'-(4'-(4-aminophenyl)imidazole) sulfinyl difluoride; 1-morpholino-1'-(4'-fluoroimidazole) sulfinyl difluoride; 1-morpholino-1'-(4'-chloroimidazole) sulfinyl difluoride; 1-morpholino-1'-(5'-methylimidazole) sulfinyl difluoride; 1-diethylamino-1'-imidazole sulfinyl difluoride; 1-diethylamino-1'-benzimidazole sulfinyl difluoride; 1-diethylamino-1'-(2'-methylimidazole) sulfinyl difluoride; 1-diethylamino-1'-(2'-ethylimidazole) sulfinyl difluoride; 1-diethylamino-1'-(2'-n-propylimidazole) sulfinyl difluoride; 1-diethylamino-1'-(2'-isopropylimidazole) sulfinyl difluoride; 1-diethylamino-1'-(2'-phenylimidazole) sulfinyl difluoride; 1-diethylamino-1'-(2'-fluoroimidazole) sulfinyl difluoride; 1-diethylamino-1'-(2'-methoxyimidazole) sulfinyl difluoride; 1-diethylamino-1'-(4'-methylimidazole) sulfinyl difluoride; 1-diethylamino-1'-(4'-phenylimidazole) sulfinyl difluoride; 1-diethylamino-1'-(4'-(2-fluorophenyl)imidazole) sulfinyl difluoride; 1-diethylamino-1'-(4'-(4-fluorophenyl)imidazole) sulfinyl difluoride; 1-diethylamino-1'-(4'-(2,4-difluorophenyl)imidazole) sulfinyl difluoride; 1-diethylamino-1'-(4'-pentafluorophenylimidazole) sulfinyl difluoride; 1-diethylamino-1'-(4'-(2chlorophenyl)imidazole) sulfinyl difluoride; 1-diethylamino-1'-(4'-(4-chlorophenyl)imidazole) sulfinyl difluoride; 1-diethylamino-1'-(4'-(2,4-dichlorophenyl)imidazole) sulfinyl difluoride; 1-diethylamino-1'-(4'-(4-methylphenyl)imidazole) sulfinyl difluoride; 1-diethylamino-1'-(4'-(4-methoxyphenyl)imidazole) sulfinyl difluoride; 1-diethylamino-1'-(4'-(4-nitrophenyl)imidazole) sulfinyl difluoride; 1-diethylamino-1'-(4'-(4-aminophenyl)imidazole) sulfinyl difluoride; 1-diethylamino-1'-(4'-fluoroimidazole) sulfinyl difluoride; 1-diethylamino-1'-(5'-methylimidazole) sulfinyl difluoride; 1-diethylamino-1'-(5'-phenylimidazole) sulfinyl difluoride; 1-diethylamino-1'-(5'-fluoroimidazole) sulfinyl difluoride; 1-dimethylamino-1'-imidazole sulfinyl difluoride; 1-dimethylamino-1'-benzimidazole sulfinyl difluoride; 1-dimethylamino-1'-(2'-methylimidazole) sulfinyl difluoride; 1-dimethylamino-1'-(2'-ethylimidazole) sulfinyl difluoride; 1-dimethylamino-1'-(2'-phenylimidazole) sulfinyl difluoride; 1-dimethylamino-1'-(2'-fluoroimidazole) sulfinyl difluoride; 1-dimethylamino-1'-(2'-chloroimidazole) sulfinyl difluoride; 1-dimethylamino-1'-(4'-methylimidazole) sulfinyl difluoride; 1-dimethylamino-1'-(4'-phenylimidazole) sulfinyl difluoride; 1-dimethylamino-1'-(4'-(2-fluorophenyl)imidazole) sulfinyl difluoride; 1-dimethylamino-1'-(4'-(4-fluorophenyl)imidazole) sulfinyl difluoride; 1-dimethylamino-1'-(4'-(2,4-difluorophenyl)imidazole) sulfinyl difluoride; 1-dimethylamino-1'-(4'-pentafluorophenylimidazole) sulfinyl difluoride; 1-dimethylamino-1'-(4'-(2-chlorophenyl)imidazole) sulfinyl difluoride; 1-dimethylamino-1'-(4'-(4-chlorophenyl)imidazole) sulfinyl difluoride; 1-dimethylamino-1'-(4'-(2,4-dichlorophenyl)imidazole) sulfinyl difluoride; 1-dimethylamino-1'-(4'-(4-methylphenyl)imidazole) sulfinyl difluoride; 1-dimethylamino-1'-(4'-(4-methoxyphenyl)imidazole) sulfinyl difluoride; 1-dimethylamino-1'-(4'-(4-nitrophenyl)imidazole) sulfinyl difluoride; 1-dimethylamino-1'-(4'-(4-aminophenyl)imidazole) sulfinyl difluoride; 1-dimethylamino-1'-(4'-fluoroimidazole) sulfinyl difluoride; 1-dimethylamino-1'-(4'-chloroimidazole) sulfinyl difluoride; 1-dimethylamino-1'-(5'-methylimidazole) sulfinyl difluoride; 1-dimethylamino-1'-(5'-phenylimidazole) sulfinyl difluoride; 1-dimethylamino-1'-(5'-fluoroimidazole) sulfinyl difluoride; 1-di(methoxyethyl)amino-1'- imidazole sulfinyl difluoride; 1-di(methoxyethyl)amino-1'-benzimidazole sulfinyl difluoride; 1-di(methoxyethyl)amino-1'-(2'-methylimidazole) sulfinyl difluoride; 1-di(methoxyethyl)amino-1'-(2'-ethylimidazole) sulfinyl difluoride; 1-di(methoxyethyl)amino-1'-(2'-n-propylimidazole) sulfinyl difluoride; 1-di(methoxyethyl)amino-1'-(2'-isopropylimidazole) sulfinyl difluoride; 1-di(methoxyethyl)amino-1'-(2'-phenylimidazole) sulfinyl difluoride; 1-di(methoxyethyl)amino-1'-(2'-fluoroimidazole) sulfinyl difluoride; 1-di(methoxyethyl)amino-1'-(2'-chloroimidazole) sulfinyl difluoride; 1-di(methoxyethyl)amino-1'-(4'-methylimidazole) sulfinyl difluoride; 1-di(methoxyethyl)amino-1'-(4'-phenylimidazole) sulfinyl difluoride; 1-di(methoxyethyl)amino-1'-(4'-(2-fluorophenyl)imidazole) sulfinyl difluoride; 1-di(methoxyethyl)amino-1'-(4'-(4-fluorophenyl)imidazole) sulfinyl difluoride; 1-di(methoxyethyl)amino-1'-(4'-(2,4-difluorophenyl)imidazole) sulfinyl difluoride; 1-di(methoxyethyl)amino-1'-(4'-pentafluorophenylimidazole) sulfinyl difluoride; 1-di(methoxyethyl)amino-1'-(4'-(2-chlorophenyl)imidazole) sulfinyl difluoride; 1-di(methoxyethyl)amino-1'-(4'-(4-chlorophenyl)imidazole) sulfinyl difluoride; 1-di(methoxyethyl)amino-1'-(4'-(2,4-dichlorophenyl)imidazole) sulfinyl difluoride; 1-di(methoxyethyl)amino-1'-(4'-(4-methylphenyl)imidazole) sulfinyl difluoride; 1-di(methoxyethyl)amino-1'-(4'-(4-methoxyphenyl)imidazole) sulfinyl difluoride; 1-di(methoxyethyl)amino-1'-(4'-(4-nitrophenyl)imidazole) sulfinyl difluoride; 1-di(methoxyethyl)amino-1'-(4'-(4-aminophenyl)imidazole) sulfinyl difluoride; 1-di(methoxyethyl)amino-1'-(4'-fluoroimidazole) sulfinyl difluoride; 1-di(methoxyethyl)amino-1'-(4'-chloroimidazole) sulfinyl difluoride; 1-di(methoxyethyl)amino-1'-(5'-methylimidazole) sulfinyl difluoride; 1-di(methoxyethyl)amino-1'-(5'-phenylimidazole) sulfinyl difluoride; 1-di(methoxyethyl)amino-1'-(5'-fluoroimidazole) sulfinyl difluoride; 1-di(methoxyethyl)amino-1'-(5'-chloroimidazole) sulfinyl difluoride; 1-diphenylamino-1'-imidazole sulfinyl difluoride; 1-diphenylamino-1'-benzimidazole sulfinyl difluoride; 1-diphenylamino-1'-(2'-methylimidazole) sulfinyl difluoride; 1-diphenylamino-1'-(2'-ethylimidazole) sulfinyl difluoride; 1-diphenylamino-1'-(2'-phenylimidazole) sulfinyl difluoride; 1-diphenylamino-1'-(2'-fluoroimidazole) sulfinyl difluoride; 1-diphenylamino-1'-(2'-chloroimidazole) sulfinyl difluoride; 1-diphenylamino-1'-(4'-methylimidazole) sulfinyl difluoride; 1-diphenylamino-1'-(4'-phenylimidazole) sulfinyl difluoride; 1-diphenylamino-1'-(4'-(2-fluorophenyl)imidazole) sulfinyl difluoride; 1-diphenylamino-1'-(4'-(4-fluorophenyl)imidazole) sulfinyl difluoride; 1-diphenylamino-1'-(4'-(2,4-difluorophenyl)imidazole) sulfinyl difluoride; 1-diphenylamino-1'-(4'-pentafluorophenylimidazole) sulfinyl difluoride; 1-diphenylamino-1'-(4'-(2-chlorophenyl)imidazole) sulfinyl difluoride; 1-diphenylamino-1'-(4'-(4-chlorophenyl)imidazole) sulfinyl difluoride; 1-diphenylamino-1'-(4'-(2,4-dichlorophenyl)imidazole) sulfinyl difluoride; 1-diphenylamino-1'-(4'-(4-methylphenyl)imidazole) sulfinyl difluoride; 1-diphenylamino-1'-(4'-(4-methoxyphenyl)imidazole) sulfinyl difluoride; 1-diphenylamino-1'-(4'-(4-nitrophenyl)imidazole) sulfinyl difluoride; 1-diphenylamino-1'-(4'-(4-aminophenyl)imidazole) sulfinyl difluoride; 1-diphenylamino-1'-(4'-fluoroimidazole) sulfinyl difluoride; 1-diphenylamino-1'-(5'-methylimidazole) sulfinyl difluoride; 1-diphenylamino-1'-(5'-phenylimidazole) sulfinyl difluoride; 1-diphenylamino-1'-(5'-fluoroimidazole) sulfinyl difluoride; 1-diethylamino-1'-(2',4'-dimethylimidazole) sulfinyl difluoride; 1-diethylamino-1'-(2',4'-diphenylimidazole) sulfinyl difluoride; 1-diethylamino-1'-(2',4'-difluoroimidazole) sulfinyl difluoride; 1-diethylamino-1'-(2',4'-dichloroimidazole) sulfinyl difluoride; 1-diethylamino-1'-(2',5'-dimethylimidazole) sulfinyl difluoride; 1-diethylamino-1'-(2',5'-diethylimidazole) sulfinyl difluoride; 1-diethylamino-1'-(2',5'-diphenylimidazole) sulfinyl difluoride; 1-diethylamino-1'-(2',5'-difluoroimidazole) sulfinyl difluoride; 1-diethylamino-1'-(2',5'-dichloroimidazole) sulfinyl difluoride; 1-diethylamino-1'-(4',5'-dicyanoimidazole) sulfinyl difluoride; 1-diethylamino-1'-(4',5'-dimethylimidazole) sulfinyl difluoride; 1-diethylamino-1'-(4',5'-diphenylimidazole) sulfinyl difluoride; 1-diethylamino-1'-(4',5'-di(2-fluorophenyl)imidazole) sulfinyl difluoride; 1-diethylamino-1'-(4',5'-di(4-fluorophenyl)imidazole) sulfinyl difluoride; 1-diethylamino-1'-(4',5'-di(2,4-difluorophenyl)imidazole) sulfinyl difluoride; 1-diethylamino-1'-(4',5'-dipentafluorophenylimidazole) sulfinyl difluoride; 1-diethylamino-1'-(4',5'-di(2-chlorophenyl)imidazole) sulfinyl difluoride; 1-diethylamino-1'-(4',5'-di(4-chlorophenyl)imidazole) sulfinyl difluoride; 1-diethylamino-1'-(4',5'-di(2,4-dichlorophenyl)imidazole) sulfinyl difluoride; 1-diethylamino-1'-(4',5'-di(4-methylphenyl)imidazole) sulfinyl difluoride; 1-diethylamino-1'-(4',5'-di(4-methoxyphenyl)imidazole) sulfinyl difluoride; 1-diethylamino-1'-(4',5'-di(4-nitrophenyl)imidazole) sulfinyl difluoride; 1-diethylamino-1'-(4',5'-di(4-aminophenyl)imidazole) sulfinyl difluoride; 1-diethylamino-1'-(4',5'-difluoroimidazole) sulfinyl difluoride; 1-dimethylamino-1'-(2',4'-dimethylimidazole) sulfinyl difluoride; 1-dimethylamino-1'-(2',4'-diphenylimidazole) sulfinyl difluoride; 1-dimethylamino-1'-(2',4'-di(2-fluorophenyl)imidazole) sulfinyl difluoride; 1-dimethylamino-1'-(2',4'-di(4-fluorophenyl)imidazole) sulfinyl difluoride; 1-dimethylamino-1'-(2',4'-di(2,4-difluorophenyl)imidazole) sulfinyl difluoride; 1-dimethylamino-1'-(2',4'-dipentafluorophenylimidazole) sulfinyl difluoride; 1-dimethylamino-1'-(2',4'-di(2-chlorophenyl)imidazole) sulfinyl difluoride; 1-dimethylamino-1'-(2',4'-di(4-chlorophenyl)imidazole) sulfinyl difluoride; 1-dimethylamino-1'-(2',4'-di(2,4-dichlorophenyl)imidazole) sulfinyl difluoride; 1-dimethylamino-1'-(2',4'-di(4-methylphenyl)imidazole) sulfinyl difluoride; 1-dimethylamino-1'-(2',4'-di(4-methoxyphenyl)imidazole) sulfinyl difluoride; 1-dimethylamino-1'-(2',4'-di(4-nitrophenyl)imidazole) sulfinyl difluoride; 1-dimethylamino-1'-(2',4'-di(4-aminophenyl)imidazole) sulfinyl difluoride; 1-dimethylamino-1'-(2',4'-difluoroimidazole) sulfinyl difluoride; 1-dimethylamino-1'-(2',4'-dichloroimidazole) sulfinyl difluoride; 1-dimethylamino-1'-(2',5'-dimethylimidazole) sulfinyl difluoride; 1-dimethylamino-1'-(2',5'-diethylimidazole) sulfinyl difluoride; 1-dimethylamino-1'-(2',5'-di-n-propylimidazole) sulfinyl difluoride; 1-dimethylamino-1'-(2',5'-diisopropylimidazole) sulfinyl difluoride; 1-dimethylamino-1'-(2',5'-diphenylimidazole) sulfinyl difluoride; 1-dimethylamino-1'-(2',5'-difluoroimidazole) sulfinyl difluoride; 1-dimethylamino-1'-(2',5'-dichloroimidazole) sulfinyl difluoride; 1-dimethylamino-1'-(4',5'-dicyanoimidazole) sulfinyl difluoride; 1-dimethylamino-1'-(4',5'-dimethylimidazole) sulfinyl difluoride;

1-dimethylamino-1'-(4',5'-diphenylimidazole) sulfinyl difluoride; 1-dimethylamino-1'-(4',5'-di(2-fluorophenyl)imidazole) sulfinyl difluoride; 1-dimethylamino-1'-(4',5'-di(4-fluorophenyl)imidazole) sulfinyl difluoride; 1-dimethylamino-1'-(4',5'-di(2,4-difluorophenyl)imidazole) sulfinyl difluoride; 1-dimethylamino-1'-(4',5'-dipentafluorophenylimidazole) sulfinyl difluoride; 1-dimethylamino-1'-(4',5'-di(2-chlorophenyl)imidazole) sulfinyl difluoride; 1-dimethylamino-1'-(4',5'-di(4-chlorophenyl)imidazole) sulfinyl difluoride; 1-dimethylamino-1'-(4',5'-di(2,4-dichlorophenyl)imidazole) sulfinyl difluoride; 1-dimethylamino-1'-(4',5'-di(4-methylphenyl)imidazole) sulfinyl difluoride; 1-dimethylamino-1'-(4',5'-di(4-methoxyphenyl)imidazole) sulfinyl difluoride; 1-dimethylamino-1'-(4',5'-di(4-nitrophenyl)imidazole) sulfinyl difluoride; 1-dimethylamino-1'-(4',5'-di(4-aminophenyl)imidazole) sulfinyl difluoride; 1-dimethylamino-1'-(4',5'-difluoroimidazole) sulfinyl difluoride; 1-dimethylamino-1'-(4',5'-dichloroimidazole) sulfinyl difluoride; 1-di(methoxyethyl)amino-1'-(2',4'-dimethylimidazole) sulfinyl difluoride; 1-di(methoxyethyl)amino-1'-(2',4'-diethylimidazole) sulfinyl difluoride; 1-di(methoxyethyl)amino-1'-(2',4'-di-n-propylimidazole) sulfinyl difluoride; 1-di(methoxyethyl)amino-1'-(2',4'-diisopropylimidazole) sulfinyl difluoride; 1-di(methoxyethyl)amino-1'-(2',4'-diphenylimidazole) sulfinyl difluoride; 1-di(methoxyethyl)amino-1'-(2',4'-di(2-fluorophenyl)imidazole) sulfinyl difluoride; 1-di(methoxyethyl)amino-1'-(2',4'-di(4-fluorophenyl)imidazole) sulfinyl difluoride; 1-di(methoxyethyl)amino-1'-(2',4'-di(2,4-difluorophenyl)imidazole) sulfinyl difluoride; 1-di(methoxyethyl)amino-1'-(2',4'-dipentafluorophenylimidazole) sulfinyl difluoride; 1-di(methoxyethyl)amino-1'-(2',4'-di(2-chlorophenyl)imidazole) sulfinyl difluoride; 1-di(methoxyethyl)amino-1'-(2',4'-di(4-chlorophenyl)imidazole) sulfinyl difluoride; 1-di(methoxyethyl)amino-1'-(2',4'-di(2,4-dichlorophenyl)imidazole) sulfinyl difluoride; 1-di(methoxyethyl)amino-1'-(2',4'-di(4-methylphenyl)imidazole) sulfinyl difluoride; 1-di(methoxyethyl)amino-1'-(2',4'-di(4-methoxyphenyl)imidazole) sulfinyl difluoride; 1-di(methoxyethyl)amino-1'-(2',4'-di(4-nitrophenyl)imidazole) sulfinyl difluoride; 1-di(methoxyethyl)amino-1'-(2',4'-di(4-aminophenyl)imidazole) sulfinyl difluoride; 1-di(methoxyethyl)amino-1'-(2',4'-difluoroimidazole) sulfinyl difluoride; 1-di(methoxyethyl)amino-1'-(2',4'-dichloroimidazole) sulfinyl difluoride; 1-di(methoxyethyl)amino-1'-(2',4'-dimethoxyimidazole) sulfinyl difluoride; 1-di(methoxyethyl)amino-1'-(2',5'-dimethylimidazole) sulfinyl difluoride; 1-di(methoxyethyl)amino-1'-(2',5'-diphenylimidazole) sulfinyl difluoride; 1-di(methoxyethyl)amino-1'-(2',5'-difluoroimidazole) sulfinyl difluoride; 1-di(methoxyethyl)amino-1'-(2',5'-dichloroimidazole) sulfinyl difluoride; 1-di(methoxyethyl)amino-1'-(4',5'-dicyanoimidazole) sulfinyl difluoride; 1-di(methoxyethyl)amino-1'-(4',5'-dimethylimidazole) sulfinyl difluoride; 1-di(methoxyethyl)amino-1'-(4',5'-diphenylimidazole) sulfinyl difluoride; 1-di(methoxyethyl)amino-1'-(4',5'-di(2-fluorophenyl)imidazole) sulfinyl difluoride; 1-di(methoxyethyl)amino-1'-(4',5'-di(4-fluorophenyl)imidazole) sulfinyl difluoride; 1-di(methoxyethyl)amino-1'-(4',5'-di(2,4-difluoro phenyl)imidazole) sulfinyl difluoride; 1-di(methoxyethyl)amino-1'-(4',5'-dipentafluorophenylimidazole) sulfinyl difluoride; 1-di(methoxyethyl)amino-1'-(4',5'-di(2-chlorophenyl)imidazole) sulfinyl difluoride; 1-di(methoxyethyl)amino-1'-(4',5'-di(4-chlorophenyl)imidazole) sulfinyl difluoride; 1-di(methoxyethyl)amino-1'-(4',5'-di(2,4-dichlorophenyl)imidazole) sulfinyl difluoride; 1-di(methoxyethyl)amino-1'-(4',5'-di(4-methylphenyl)imidazole) sulfinyl difluoride; 1-di(methoxyethyl)amino-1'-(4',5'-di(4-methoxyphenyl)imidazole) sulfinyl difluoride; 1-di(methoxyethyl)amino-1'-(4',5'-di(4-nitrophenyl)imidazole) sulfinyl difluoride; 1-di(methoxyethyl)amino-1'-(4',5'-di(4-aminophenyl)imidazole) sulfinyl difluoride; 1-di(methoxyethyl)amino-1'-(4',5'-difluoroimidazole) sulfinyl difluoride; 1-di(methoxyethyl)amino-1'-(4',5'-dichloroimidazole) sulfinyl difluoride; 1-diphenylamino-1'-(2',4'-dimethylimidazole) sulfinyl difluoride; 1-diphenylamino-1'-(2',4'-diphenylimidazole) sulfinyl difluoride; 1-diphenylamino-1'-(2',4'-di(2-fluorophenyl)imidazole) sulfinyl difluoride; 1-diphenylamino-1'-(2',4'-di(4-fluorophenyl)imidazole) sulfinyl difluoride; 1-diphenylamino-1'-(2',4'-di(2,4-difluorophenyl)imidazole) sulfinyl difluoride; 1-diphenylamino-1'-(2',4'-dipentafluorophenylimidazole) sulfinyl difluoride; 1-diphenylamino-1'-(2',4'-di(2-chlorophenyl)imidazole) sulfinyl difluoride; 1-diphenylamino-1'-(2',4'-di(4-chlorophenyl)imidazole) sulfinyl difluoride; 1-diphenylamino-1'-(2',4'-di(2,4-dichlorophenyl)imidazole) sulfinyl difluoride; 1-diphenylamino-1'-(2',4'-di(4-methylphenyl)imidazole) sulfinyl difluoride; 1-diphenylamino-1'-(2',4'-di(4-methoxyphenyl)imidazole) sulfinyl difluoride; 1-diphenylamino-1'-(2',4'-di(4-nitrophenyl)imidazole) sulfinyl difluoride; 1-diphenylamino-1'-(2',4'-di(4-aminophenyl)imidazole) sulfinyl difluoride; 1-diphenylamino-1'-(2',4'-difluoroimidazole) sulfinyl difluoride; 1-diphenylamino-1'-(2',4'-di(fluoromethyl)imidazole) sulfinyl difluoride; 1-diphenylamino-1'-(2',4'-dichloroimidazole) sulfinyl difluoride; 1-diphenylamino-1'-(2',5'-dimethylimidazole) sulfinyl difluoride; 1-diphenylamino-1'-(2',5'-diphenylimidazole) sulfinyl difluoride; 1-diphenylamino-1'-(2',5'-difluoroimidazole) sulfinyl difluoride; 1-diphenylamino-1'-(2',5'-dichloroimidazole) sulfinyl difluoride; 1-diphenylamino-1'-(4',5'-dicyanoimidazole) sulfinyl difluoride; 1-diphenylamino-1'-(4',5'-dimethylimidazole) sulfinyl difluoride; 1-diphenylamino-1'-(4',5'-diphenylimidazole) sulfinyl difluoride; 1-diphenylamino-1'-(4',5'-di(2-fluorophenyl)imidazole) sulfinyl difluoride; 1-diphenylamino-1'-(4',5'-di(4-fluorophenyl)imidazole) sulfinyl difluoride; 1-diphenylamino-1'-(4',5'-di(2,4-difluorophenyl)imidazole) sulfinyl difluoride; 1-diphenylamino-1'-(4',5'-dipentafluorophenylimidazole) sulfinyl difluoride; 1-diphenylamino-1'-(4',5'-di(2-chlorophenyl)imidazole) sulfinyl difluoride; 1-diphenylamino-1'-(4',5'-di(4-chlorophenyl)imidazole) sulfinyl difluoride; 1-diphenylamino-1'-(4',5'-di(2,4-dichlorophenyl)imidazole) sulfinyl difluoride; 1-diphenylamino-1'-(4',5'-di(4-methylphenyl)imidazole) sulfinyl difluoride; 1-diphenylamino-1'-(4',5'-di(4-methoxyphenyl)imidazole) sulfinyl difluoride; 1-diphenylamino-1'-(4',5'-di(4-nitrophenyl)imidazole) sulfinyl difluoride; 1-diphenylamino-1'-(4',5'-di(4-aminophenyl)imidazole) sulfinyl difluoride; 1-diphenylamino-1'-(4',5'-difluoroimidazole) sulfinyl difluoride; 1-diphenylamino-1'-(4',5'-dichloroimidazole) sulfinyl difluoride; 1-morpholino-1'-(trichloroimidazole) sulfinyl difluoride; 1-morpholino-1'-(trifluoroimidazole) sulfinyl difluoride; 1-morpholino-1'-(trimethylimidazole) sulfinyl difluoride; 1-morpholino-1'-(triphenylimidazole) sulfinyl difluoride; 1-diethylamino-1'-(trichloroimidazole) sulfinyl difluoride; 1-diethylamino-1'-(trifluoroimidazole) sulfinyl difluoride; 1-diethylamino-1'-(trimethylimidazole) sulfinyl difluoride; 1-diethylamino-1'-

(triphenylimidazole) sulfinyl difluoride; 1-dimethylamino-1'-(trichloroimidazole) sulfinyl difluoride; 1-dimethylamino-1'-(trifluoroimidazole) sulfinyl difluoride; 1-dimethylamino-1'-(trimethylimidazole) sulfinyl difluoride; 1-dimethylamino-1'-(triphenylimidazole) sulfinyl difluoride; 1-di(methoxyethyl)amino-1'-(trichloroimidazole) sulfinyl difluoride; 1-di(methoxyethyl)amino-1'-(trifluoroimidazole) sulfinyl difluoride; 1-di(methoxyethyl)amino-1'-(trimethylimidazole) sulfinyl difluoride; 1-di(methoxyethyl)amino-1'-(triphenylimidazole) sulfinyl difluoride; 1-diphenylamino-1'-(trichloroimidazole) sulfinyl difluoride; 1-diphenylamino-1'-(trifluoroimidazole) sulfinyl difluoride; 1-diphenylamino-1'-(trimethylimidazole) sulfinyl difluoride; and 1-diphenylamino-1'-(triphenylimidazole) sulfinyl difluoride.

The following non-limiting examples illustrate the preparative method, physical and chemical properties, and utility of some of these compounds. Examples 1–3 describe the synthesis of three typical trimethylsilylimidazole precursors. Examples A–C describe three individual synthesis of bis(imidazole)sulfur difluoride compositions of Structure (I). Example D describes the synthesis of a representative compound of Structure (II). Examples I–III describe applications of these new compounds as deoxofluorination agents.

EXAMPLE 1

Preparation of 1-Trimethylsilyl-4,5-dichloroimidazole

Into a 100 mL 3 neck round bottom flask fitted with a dropping funnel, nitrogen inlet tube, and gas exit tube was loaded 4,5-dichloroimidazole, 5.08 g (37.1 mmol) and 50 mL anhydrous $CH_3CN$. To this solution was added in five minutes hexamethyldisilazane, 4.50 g (27.9 mmol), under nitrogen and with stirring. The resulting mixture was refluxed for 20 hours under nitrogen. After the specified time, the flask and contents were cooled slightly, the flask was fitted with a fractional distillation head, and then heating continued. The first liquid fraction was collected at 80° C. at ambient pressure. When the last amount of the first liquid fraction had been collected, the system was put under 0.2 Torr vacuum and heating was continued. The second liquid fraction was collected at 114° C. (0.2 Torr) and weighed 6.96 g (89.8%). The product was subsequently handled in a nitrogen atmosphere. Analysis of the product by NMR ($CD_2Cl_2$) was consistent with the desired product at greater than 97.3% purity.

Analysis $^1$H NMR: d 7.28 ppm (1 H, s) and d 0.49 ppm (9 H, s); $^{13}$C NMR: d 137.95 ppm (1 C, s), d 127.95 ppm (1 C, s), d 115.26 ppm (1 C, s), and d –0.81 ppm (3 C, s). MS m/e (%): 208 (5%, M$^+$), 136 (15%), 109 (15%), 73 (100%). Anal. Calcd for $C_6H_{10}Cl_2N_2Si$: C(34.46); H(4.82); N(13.39); Cl (33.90); Si (13.43). Found: C(34.30); H(4.45); N(13.61); Cl (33.74); Si (11.46).

EXAMPLE 2

Preparation of 1-Trimethylsilyl-4-phenylimidazole

Into a 100 mL 3 neck round bottom flask fitted with a dropping funnel, nitrogen inlet tube, and gas exit tube was loaded 4-phenylimidazole, 5.08 g (35.2 mmol), and 75 mL anhydrous $CH_3CN$. To this slurry was added in five minutes hexamethyldisilazane, 4.40 g (27.3 mmol), under nitrogen and with stirring. The resulting slurry was stirred for 1 hour at room temperature after which time it became homogeneous and clear. The solution was then refluxed for 20 hours under nitrogen. After the specified time, the flask and contents were cooled slightly, the flask was fitted with a fractional distillation head, and then heating continued. The first liquid fraction was collected at 80° C. at ambient pressure. When the last amount of the first liquid fraction had been collected, the system was put under 0.2 Torr vacuum and heating was continued. The second liquid fraction was collected at 147–150° C. (0.2 Torr). ). Analysis of this fraction was consistent with the desired product and weighed 6.71 g (88.1%).

Analysis $^1$H NMR: d 7.68 ppm (1 H, s), d 7.39 ppm (1 H, s), d 7.96 ppm (2 H, dm, $J_{HH}$=8.3, 1.4 Hz), d 7.45 ppm (2 H, tm, $J_{HH}$=7.6, 1.5 Hz), d 7.30 ppm (1 H, tt, $J_{HH}$=7.4, 1.5 Hz), d 0.52 ppm (9 H, $^2J_{HSi}$=6.9 Hz), $^{13}$C NMR: d 143.91 ppm (1 C, s), d 116.12 ppm (1 C, s), d 140.63 ppm (1 C, s), d 134.92 ppm (1 C, s), d 128.80 ppm (2 C, s), d 126.72 ppm (1 C, s), d 125.16 ppm (2 C, s), and d –0.52 ppm (3 C, s*, $^1J_{HSi}$=28.8 Hz). MS m/e (%): 216 (24%, M$^+$), 143 (5%), 116 (21%), 73 (100%). Anal. Calcd for $C_{12}H_{16}N_2Si$: C(66.62); H(7.45); N(12.95); Si (12.98). Found: C(66.16); H(7.19); N(12.86); Si (11.44).

EXAMPLE 3

Preparation of 1-Trimethylsilyl-4-methylimidazole

Into a 100 mL 3 neck round bottom flask fitted with a dropping funnel, nitrogen inlet tube, and gas exit tube was loaded 4-methylimidazole, 6.51 g (79.3 mmol) and 75 mL anhydrous $CH_3CN$. To this yellow solution was added in five minutes hexamethyldisilazane, 9.83 g (60.9 mmol), under nitrogen and with stirring. The resulting solution was then refluxed for 18 hours under nitrogen. After the specified time, the flask and contents were cooled slightly, the flask was fitted with a fractional distillation head, and then heating continued. The first liquid fraction was collected at 80° C. at ambient pressure. When the last amount of the first liquid fraction had been collected, the system was put under 0.2 Torr vacuum and heating was continued. The second liquid fraction was collected at 150° C. (0.2 Torr). Analysis of this fraction was consistent with the desired product and weighed 9.76 g (80%).

Analysis $^1$H NMR: d 7.42 ppm (1 H, s), d 6.67 ppm (1 H, s), d 2.19 ppm (3 H, s), and d 0.39 ppm (9 H, s); $^{13}$C NMR: d 139.27 ppm (1 C, s), d 138.77 ppm (1 C, s), d 117.28 ppm (1 C, s), d 13.20 ppm (1 C, s), and d –0.55 ppm (3 C, s*, $^1J_{HSi}$=28.8 Hz). MS m/e (%): 154 (24%, M$^+$), 139 (6%), 112 (9%), 98 (10%), 84 (13%), 73 (100%). Anal. Calcd for $C_7H_{14}N_2Si$: C(54.49); H(9.15); N(18.16); Si (18.20). Found: C(52.94); H(8.73); N(18.19); Si (11.83).

EXAMPLE A

Preparation of Bis(imidazole)Sulfur Difluoride from 1-Trimethylsilylimidazole and Sulfur Tetrafluoride In the dry nitrogen atmosphere of a glovebox, a dropping funnel was loaded with a solution containing 4.95 g (35.3 mmol) of 1-trimethylsilylimidazole and 25 mL of $P_4O_{10}$-dried $CFCl_3$. The dropping funnel was then connected to a 100 mL 3-neck round bottom flask. Approximately 25 mL of $P_4O_{10}$-dried $CFCl_3$ was then transferred to the flask, a magnetic stir bar was added, and the remaining two necks of the flask were subsequently connected with an on/off valve and a dry-ice condenser. The entire apparatus was removed from the glovebox. The flask portion was immersed in a dry-ice/acetone bath at −78° C., stirring was initiated, and then SF$_4$, 6.5 g (60 mmol), was condensed into the flask. The solution of trimethysilylimidazole in CFCl$_3$ was then added dropwise to the stirred solution of SF$_4$ in CFCl$_3$ over the course of 15 minutes. The solution was then stirred for an additional hour at −78° C. and then warmed to −63° C. The −63° C. solution was then pumped on using good vacuum for 35 minutes and then warmed to −12° C. at which temperature it was pumped on with good vacuum for an additional 45 minutes. The flask and contents were then warmed to room temperature and pumped on until all volatiles had been removed. The resulting pale-yellow free-flowing solid was transferred to the dry nitrogen atmosphere of a glovebox where all subsequent manipulations on the solid were conducted.

Analysis of this pale-yellow solid by NMR, MS, and elemental analysis was consistent with the proposed structure of bis(imidazole)sulfur difluoride. The solid weighed approximately 3.5 g which corresponds to an isolated yield of 97.5% based on the starting imidazole derivative.

Analysis

Yellow solid, m.p. 93.5–95° C.; NMR (CDCl$_3$ solution), $^1$H: d 8.06 ppm (1 H, m, J=0.95 Hz), d 7.42 ppm (1 H, m, J=1.84 Hz), d 7.06 ppm (1 H, m, J=0.80 Hz); $^{13}$C{$^1$H}: d 137.86 ppm (1 C, t, J=9.8 Hz), d 130.34 ppm (1 C, s), d 119.01 ppm (1 C, t, J=7.6 Hz); $^{19}$F d 47.81 ppm (2 F, br s). MS m/e (%): 204 (2.4%, M$^+$), 185 (16%),137 (100%). Anal. Calcd for C$_6$H$_6$F$_2$N$_4$S : C(35.29); H(2.96); F(18.61); N(27.44); S(15.70). Found: C(34.90); H(2.66); F(17.66); N(25.33); S(14.25).

EXAMPLE B

Preparation of Bis(imidazole)Sulfur Difluoride Directly from Imidazole and Sulfur Tetrafluoride This example describes an alternative method of preparing the imidazole sulfur difluoride compounds which entails a direct reaction between the free amine of the corresponding imidazole with sulfur tetrafluoride in the presence of an HF scavenger. Thus, in the dry nitrogen atmosphere of a glovebox, a dropping funnel was loaded with a solution containing 3.639 g (53.5 mmol) of imidazole and 50 mL of anhydrous CH$_2$Cl$_2$. The dropping funnel was then connected to a 100 mL 3-neck round bottom flask. Approximately 30 mL of anhydrous CH$_2$Cl$_2$ and dry NaF, 5.5 g (131 mmol), was transferred to the flask, a magnetic stir bar was added, and the remaining two necks of the flask were subsequently connected with an on/off valve and a dry-ice condenser. The entire apparatus was removed from the glovebox. The flask portion was immersed in a dry-ice/acetone bath at −78° C., stirring was initiated, and then SF$_4$, 15.2 g (141 mmol), was condensed into the flask. The solution of imidazole in CH$_2$Cl$_2$ was then added dropwise to the stirred solution of SF$_4$ in CH$_2$Cl$_2$ over the course of 59 minutes. The solution was then stirred for an additional 45 minutes at −78° C. and then allowed to warm to room temperature overnight with stirring. The resulting white slurry was transferred to the dry nitrogen atmosphere of a glovebox and filtered; filtration afforded a pale-yellow solution which, upon evaporation to dryness, afforded a pale-yellow solid weighing 1.90 g. Results of the analysis of this solid by NMR were consistent with those expected for bis(imidazole)sulfur difluoride.

EXAMPLE C

Preparation of Bis(4-phenylimidazole)Sulfur Difluoride from 1-Trimethylsilyl-4-phenylimidazole and Sulfur Tetrafluoride In the dry nitrogen atmosphere of a glovebox, a dropping funnel was loaded with a solution containing 5.201 g (24.0 mmol) of 1-trimethylsilyl-4-phenylimidazole and 35 mL of P$_4$O$_{10}$-dried CFCl$_3$. The dropping funnel was then connected to a 100 mL 3-neck round bottom flask. Approximately 40 mL of P$_4$O$_{10}$-dried CFCl$_3$ was then transferred to the flask, a magnetic stir bar was added, and the remaining two necks of the flask were subsequently connected with an on/off valve and a dry-ice condenser. The entire apparatus was removed from the glovebox. The flask portion was immersed in a dry-ice/acetone bath at −78° C., stirring was initiated, and then SF$_4$, 5.4 g (50 mmol), was condensed into the flask. The solution of trimethysilyl-4-phenylimidazole in CFCl$_3$ was then added dropwise to the stirred solution of SF$_4$ in CFCl$_3$ over the course of 15 minutes. The reaction mixture was then stirred for two additional hours at −78° C. and then warmed to −32° C. with stirring over the course of 60 minutes. The reaction mixture was then warmed to 0° C. and pumped on using good vacuum for 60 minutes. The flask and contents were then warmed to room temperature and pumped on until all volatiles had been removed. The resulting white free-flowing solid was transferred to the dry nitrogen atmosphere of a glovebox where all subsequent manipulations on the solid were conducted.

Analysis of this white free-flowing solid by NMR, MS, and elemental analysis was consistent with the proposed structure of bis(4-phenylimidazole)sulfur difluoride. The solid weighed approximately 3.21 g which corresponds to an isolated yield of 75% based on the starting imidazole derivative.

Analysis

White solid, m.p. 133–134° C.; NMR (CDCl$_3$ solution), $^1$H: d 8.22 ppm (m), d 7.76 ppm (m), d 7.32 ppm (m); $^{13}$C{$^1$H}: d 143.23 ppm (1 C, s), d 138.24 ppm (1 C, t, J=10.1 Hz), d 131.87 ppm (1 C, s), d 128.78 ppm (2 C, s), d 128.37 ppm (1 C, s), d 125.30 ppm (2 C, s), d 113.65 ppm (1 C, t, J=8.0 Hz); $^{19}$F d 47.22 ppm (2 F, br s). MS m/e (%): 213 (2.0%), 144 (100%). Anal. Calcd for C$_{18}$H$_{14}$F$_2$N$_4$S: C(60.66); H(3.96); F(10.66); N(15.72); S(9.00). Found: C(60.48); H(4.43); F(9.41); N(15.70); S(8.63).

EXAMPLE D

Preparation of Imidazole Morpholino Sulfur Difluoride from 1-Trimethylsilylimidazole and Morpholinosulfur Trifluoride Under a dry nitrogen atmosphere a 100 mL roundbottom flask was loaded with a solution of 4.72 g (26.9 mmol) morpholinosulfur trifluoride in 30 mL of anhydrous CH$_2$Cl$_2$. The flask and contents were cooled to 0° C. under nitrogen and then a solution containing 3.66 g (26.1 mmol) 1-trimethylsilylimidazole in 30 mL of anhydrous CH$_2$Cl$_2$ was added dropwise with stirring over the period of twenty minutes. The resulting brown solution containing some crystalline material was analyzed directly by NMR spectroscopy. The NMR spectra so obtained were consistent with the proposed structure of imidazole morpholino sulfur difluoride.

Analysis

NMR (neat solution, D$_2$O cap), $^1$H: d 7.80 ppm (1H, m), d 7.25 ppm (1H, m), d 6.95 ppm (1H, m), $^1$H: d 3.49 ppm (4H, m, J=4.0 Hz), d 2.99 ppm (4H, m, J=4.0 Hz); $^{13}$C{$^1$H}: d 142.96 ppm (1 C, s), d 138.16 ppm (1 C, s), d 129.03 ppm (1 C, s), d 66.42 ppm (2 C, s), d 55.30 ppm (2 C, s); $^{19}$F d 32.77 ppm (2 F, br s).

EXAMPLE I

The Use of Bis(imidazole)Sulfur Difluoride for the Preparation of 4-Fluoro-t-butylcyclohexane by Deoxofluorination A solution of bis(imidazole)sulfur difluoride in CDCl$_3$ was treated at room temperature with an excess of 4-t- butylcyclohexanol. The resulting mixture was analyzed by NMR spectroscopy which revealed a product distribution containing both the desired fluorinated product (87%) as well as the elimination product (13%).

Relative amounts were 87% 4-fluoro-t-butylcyclohexane as a mixture of axial and equatorial fluoroisomers (ax/eq= 1.2), $^{19}F_{eq}$ d −169.29 ppm (1 F, d, J=49.3 Hz) and $^{19}F_{ax}$ d −185.31 ppm (1 F, m, J=48.8 Hz) and 13% 4-t-butylcyclohex-1-ene which represents the elimination product.

EXAMPLE II

The Use of Bis(imidazole)Sulfur Difluoride for the Preparation of Fluorocyclooctane by Deoxofluorination A solution of bis(imidazole)sulfur difluoride in $CH_3CN/CDCl_3$ was treated at room temperature with an excess of cyclooctanol. The resulting mixture was analyzed by NMR spectroscopy which revealed a product distribution containing the desired fluorinated product, fluorocyclooctane as well as the elimination product, cyclooctene.

Relative molar amounts were 93% fluorocyclooctane, $^{19}F_{eq}$ d −159.49 ppm (1 F, d, coupling not resolved), $^1H$ d 4.55 ppm (1 H, m, coupling not resolved); and 7% cyclooct-1-ene, $^1H$ d 5.49 ppm (1 H, m, coupling not resolved) which represents the elimination product.

EXAMPLE III

The Use of Bis(imidazole)Sulfur Difluoride for the Preparation of Fluorocyclooctane by Deoxofluorination A solution of bis(imidazole)sulfur difluoride, 1.35 g (6.6 mmol), in 50 mL of anhydrous $CH_2Cl_2$, was prepared in a 2-neck 100-mL roundbottom flask in an argon/nitrogen purged glovebox. The solution was cooled to −78° C. under argon with stirring and then treated with a solution of cyclooctanol, 0.57 g (4.5 mmol), added dropwise over a five minute period. The stirred solution was allowed to warm slowly to room temperature overnight. After the specified time, the reaction mixture was poured into 50 mL of saturated aqueous $NaHCO_3$. The resulting aqueous mixture was extracted with 3×50 mL portions of $CH_2Cl_2$ and the combined methylene chloride extracts were dried ($MgSO_4$) and then evaporated down to a yellow liquid product containing a small amount of white solid material. The total product weighed 0.61 grams. Analysis of this product by NMR spectroscopy in $CDCl_3$ revealed an absence of cyclooctanol indicating 100% conversion had been obtained, and a product distribution containing the desired fluorinated product, fluorocyclooctane as well as the elimination product, cyclooctene. Relative molar amounts were the same as obtained in Example II above, i.e., 93% fluorocyclooctane, $^{19}F_{eq}$ d −159.61 ppm (1 F, d, coupling not resolved), $^1H$ d 4.62 ppm (1 H, m, coupling not resolved); and 7% cyclooct-1-ene, $^1H$ d 5.54 ppm (1 H, m, coupling not resolved) which represents the elimination product.

The new sulfur(IV) difluoride compounds of the present invention are effective deoxofluorination agents, which are safe to handle and use. These compounds are easily handled solids which melt at high temperature and are thermally stable beyond their melting points. Thermal decomposition of these compounds occurs slowly and without the rapid release of gaseous by-products which is generally associated with explosive materials. By comparison to other similar sulfur-fluorine compounds wherein the decomposition is generally accompanied by a rapid and uncontrollable release of gaseous pressure, these new compounds are inherently much safer to handle and use, and therefore, represent a unique and surprising advance in the field of deoxofluorination.

The present invention has been set forth with regard to several preferred embodiments, but the full scope of the present invention should be ascertained from the claims which follow.

I claim:

1. A compound having the structure:

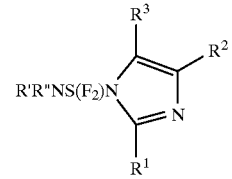

wherein $R^{1-3}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, and a $C_{4-8}$ saturated cyclic hydrocarbon having 1–3 heteroatoms selected from the group consisting of oxygen, nitrogen, sulfur, and mixtures thereof; and $R^{2-3}$ together are:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical;

wherein R' and R" are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, and $C_{4-10}$ heteroaryl or when taken together with the nitrogen group form a saturated cyclic ring having 2–10 carbon ring members and 0–2 heteroatoms selected from the group consisting of oxygen, nitrogen, sulfur, and mixtures thereof; and R' and R" together are an imidazole ring of the formula:

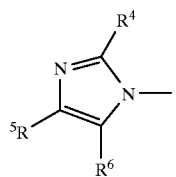

having $R^{4-6}$ which are the same or different than $R^{1-3}$ on the other imidazole ring and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, and a $C_{4-8}$ saturated cyclic hydrocarbon having 1–3 heteroatoms selected from the group consisting of oxygen, nitrogen, sulfur, and mixtures thereof; and $R^{5-6}$ together are:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

2. The compound of claim 1 wherein the compound has the structure:

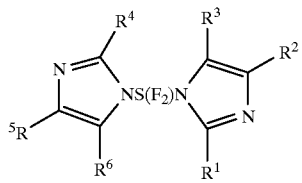

wherein $R^{1-6}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, and a $C_{4-8}$ saturated cyclic hydrocarbon having 1–3 heteroatoms selected from the group consisting of oxygen, nitrogen, sulfur, and mixtures thereof; and $R^{2-3}$ and $R^{5-6}$ respectively are:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

3. The compound of claim 1 which is 1,1'-Di(imidazole) Sulfinyl Difluoride.

4. The compound of claim 1 which is 1,1'-Di(4-phenylimidazole) Sulfinyl Difluoride.

5. The compound of claim 1 which is 1-morpholino-1'-imidazole Sulfinyl Difluoride.

6. A method for fluorination of a first compound using a fluorinating reagent comprising contacting said first compound with said fluorinating reagent under conditions sufficient to fluorinate said first compound wherein said fluorinating reagent is a second compound having the structure:

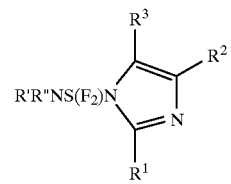

wherein $R^{1-3}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, and a $C_{4-8}$ saturated cyclic hydrocarbon having 1–3 heteroatoms selected from the group consisting of oxygen, nitrogen, sulfur, and mixtures thereof; and $R^{2-3}$ together are:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical;

wherein R' and R" are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, and $C_{4-10}$ heteroaryl or when taken together with the nitrogen group form a saturated cyclic ring having 2–10 carbon ring members and 0–2 heteroatoms selected from the group consisting of oxygen, nitrogen, sulfur, and mixtures thereof; and R' and R" together are an imidazole ring of the formula:

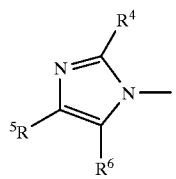

having $R^{4-6}$ which are the same or different than $R^{1-3}$ on the other imidazole ring and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, and a $C_{4-8}$ saturated cyclic hydrocarbon having 1–3 heteroatoms selected from the group consisting of oxygen, nitrogen, sulfur, and mixtures thereof; and $R^{5-6}$ together are:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

7. The method of claim 6 wherein the second compound has the structure:

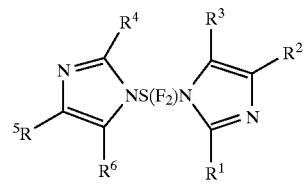

wherein $R^{1-6}$ are the same or different and are selected from the group consisting of hydrogen, halogen, $C_{1-8}$ alkyl, $C_{1-8}$ haloalkyl, alkoxyalkyl where the alkoxy portion is $C_{1-3}$ and the alkyl portion is $C_{1-8}$, haloalkoxyalkyl where the haloalkoxy portion is $C_{1-3}$ and the alkyl portion is $C_{1-8}$, haloalkoxyhaloalkyl where the haloalkoxy portion is $C_{1-3}$ and the haloalkyl portion is $C_{1-8}$, $C_{4-10}$ aryl, $C_{4-10}$ haloaryl, alkylaryl where the alkyl portion is $C_{1-8}$ and the aryl portion is $C_{4-10}$, alkoxyaryl where the alkoxy portion is $C_{1-3}$ and the aryl portion is $C_{4-10}$, alkoxyalkylaryl where the alkoxy and alkyl portions each are $C_{1-3}$ and the aryl portion is $C_{4-10}$, $C_{4-10}$ heteroaryl, cyano, nitro, amino, sulfonic acid, sulfonic methyl ester, and a $C_{4-8}$ saturated cyclic hydrocarbon having 1–3 heteroatoms selected from the group consisting of oxygen, nitrogen, sulfur, and mixtures thereof; and $R^{2-3}$ and $R^{5-6}$ respectively are:

(a) a cyclic ring having 2–10 carbon ring members and 1 heteroatom selected from the group consisting of oxygen, sulfur, nitrogen, $C_{1-3}$ alkylated nitrogen, hydrogenated nitrogen, and halogenated nitrogen; or (b) an unsaturated cyclic ring with 2 to 4 carbon atoms and 0–3 heteroatoms selected from the group consisting of oxygen, sulfur, nitrogen, $C_{1-3}$ alkylated nitrogen, hydrogenated nitrogen, and halogenated nitrogen; or (c) a fused $C_{4-10}$ aryl, alkylaryl where the alkyl portion is $C_{1-3}$ and the aryl portion is $C_{4-10}$, haloalkylaryl where the haloalkyl portion is $C_{1-3}$ and the aryl portion is $C_{4-10}$, or $C_{4-10}$ haloaryl radical.

8. The method of claim 6 wherein said first compound is selected from the group consisting of alcohols, carboxylic acids, aldehydes, ketones, carboxylic acid halides, sulfoxides, phosphonic acides, sulfinyl halides, sulfonic acids, sulfonylhalides, silylhalides, silylethers of alcohols, epoxides, phosphines, thiophosphines, sulfides and mixtures thereof.

9. The method of claim 6 wherein said second compound is 1,1'-Di(imidazole)Sulfinyl Difluoride.

10. The method of claim 6 wherein said second compound is 1,1'-Di(4-phenylimidazole) Sulfinyl Difluoride.

11. The method of claim 6 wherein said second compound is 1-morpholino-1'-imidazole Sulfinyl Difluoride.

* * * * *